(12) United States Patent
Satou et al.

(10) Patent No.: US 9,765,173 B2
(45) Date of Patent: Sep. 19, 2017

(54) COMPOUND CONTAINING PHENOLIC HYDROXYL GROUP, PHENOLIC RESIN, CURABLE COMPOSITION, CURED PRODUCT THEREOF, SEMICONDUCTOR SEALING MATERIAL, AND PRINTED CIRCUIT BOARD

(71) Applicant: DIC Corporation, Tokyo (JP)

(72) Inventors: Yutaka Satou, Ichihara (JP); Ayumi Takahashi, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 14/900,296

(22) PCT Filed: Feb. 27, 2014

(86) PCT No.: PCT/JP2014/054920
§ 371 (c)(1),
(2) Date: Dec. 21, 2015

(87) PCT Pub. No.: WO2014/208132
PCT Pub. Date: Dec. 31, 2014

(65) Prior Publication Data
US 2016/0369032 A1    Dec. 22, 2016

(30) Foreign Application Priority Data
Jun. 26, 2013    (JP) ................. 2013-133783

(51) Int. Cl.
*C08G 8/00* (2006.01)
*C07D 307/92* (2006.01)
(Continued)

(52) U.S. Cl.
CPC ............ *C08G 8/02* (2013.01); *C07D 307/77* (2013.01); *C07D 307/92* (2013.01); *C08L 63/04* (2013.01);
(Continued)

(58) Field of Classification Search
None
See application file for complete search history.

(56) References Cited

U.S. PATENT DOCUMENTS 5,458,814 A    10/1995 Kumar et al.
5,573,712 A    11/1996 Kumar et al.
(Continued)

FOREIGN PATENT DOCUMENTS

| JP | 11-140277 A | 5/1999 |
| JP | 11-510815 A | 9/1999 |
| JP | 2006-503797 A | 2/2006 |

OTHER PUBLICATIONS

Hogberg (Acta Chemica Scandinavica 26 (1972) 309-316).*
(Continued)

*Primary Examiner* — Vu A Nguyen
(74) *Attorney, Agent, or Firm* — Locke Lord LLP (57) ABSTRACT

There are provided a compound containing a phenolic hydroxyl group which exhibits excellent heat resistance and excellent flame retardancy in terms of a cured product, a phenolic resin including the same, a curable composition and a cured product thereof, and a semiconductor sealing material. The compound containing a phenolic hydroxyl group has a dinaphthofuran skeleton, in which each of the two naphthylene skeletons has a hydroxyl group on an aromatic nucleus thereof.

8 Claims, 1 Drawing Sheet

(51) Int. Cl.
| | |
|---|---|
| H01L 23/29 | (2006.01) |
| H05K 1/03 | (2006.01) |
| C08G 8/02 | (2006.01) |
| C07D 307/77 | (2006.01) |
| C08L 63/04 | (2006.01) |
| H05K 1/09 | (2006.01) |
| C08L 61/04 | (2006.01) |

(52) U.S. Cl.
CPC ......... *H01L 23/295* (2013.01); *H05K 1/0326* (2013.01); *H05K 1/09* (2013.01); *C08L 61/04* (2013.01)

(56) References Cited

U.S. PATENT DOCUMENTS

| | | |
|---|---|---|
| 5,650,098 A | 7/1997 | Kumar et al. |
| 5,651,923 A | 7/1997 | Kumar et al. |
| 2003/0171427 A1 | 9/2003 | Eder et al. |

OTHER PUBLICATIONS

Högberg, Hans E., "Cyclooligomerization of Quinones. III. Action of Strong Acids on 1,4-Naphthoquinone," Acta Chemica Scandinavica, 1972, vol. 26, No. 1, pp. 309-316.

Gomes, Louis Mavoungou, "Naphtho[2,3-b]furans, Comptes Rendus des Seances de l'Academie des Sciences," Serie C: Sciences Chimiques, 1970, vol. 270, No. 8, pp. 750-753.

Arienti, Attilio et al, "Highly selective conversion of hydroxylated biaryls to dibenzofuran derivatives over zeolite catalyst," Journal of the Chemical Society, Perkin Transactions 1: Organic and Rio-Organic Chemistry, 1997, No. 9, pp. 1391-1393.

Cameron, Donald W. et al, "Synthesis of a natural polychloro dinaphthofuran quinone," Tetrahedron Letters, 1980, vol. 21, No. 14, pp. 1385-1386.

Fales, H. M., "Unusual Oxidation of a Dinaphthofuran," Liebigs Annalen der Chemie, 1983, No. 3, pp. 367-371 and a cover page.

International Search Report mailed May 27, 2014, issued for PCT/JP2014/054920.

* cited by examiner

COMPOUND CONTAINING PHENOLIC HYDROXYL GROUP, PHENOLIC RESIN, CURABLE COMPOSITION, CURED PRODUCT THEREOF, SEMICONDUCTOR SEALING MATERIAL, AND PRINTED CIRCUIT BOARD

TECHNICAL FIELD

The present invention relates to a compound containing a phenolic hydroxyl group which exhibits excellent heat resistance and flame retardancy in terms of a cured product thereof, a phenolic resin including the same, a curable composition and a cured product thereof, a semiconductor sealing material, and a printed circuit board.

BACKGROUND ART

A phenolic resin has been used, for example, as a curing agent for epoxy resins, and an epoxy resin composition which is cured by a phenolic resin as a curing agent is widely used in electrical and electronic fields such as a semiconductor sealing material and a printed circuit board insulating material from the viewpoint that the cured product has excellent heat resistance and moisture resistance, in addition to an adhesive, a molding material, and a coating material.

Among these, a power semiconductor represented by a power module for an automobile is a technology crucial to energy saving in electrical and electronic equipment, and with a larger current, miniaturization, and high efficiency of a power semiconductor, transition from a silicon (Si) semiconductor in the related art to a silicon carbide (SiC) semiconductor has been advancing. The advantage of the SiC semiconductor is that the SiC semiconductor can be operated under higher temperature conditions, and therefore, a semiconductor sealing material is required to have higher heat resistance than those of semiconductor sealing materials in the related art. In addition, it is also important for the required performance of a semiconductor sealing resin to exhibit high flame retardancy without using a halogen-based flame retardant, and a resin material which has such performance has been required.

As the resin material to cope with these various required characteristics, for example, the phenolic resin represented by the following structural formula is known (refer to PTL 1).

[Chem. 1]

Such a phenolic resin exhibits excellent flame retardancy in terms of the cured product; however, does not have sufficient heat resistance.

CITATION LIST

Patent Literature

[PTL 1] JP-A-11-140277

SUMMARY OF INVENTION

Technical Problem

Therefore, an object of the present invention is to provide a compound containing a phenolic hydroxyl group, which exhibits excellent heat resistance and flame retardancy in terms of a cured product thereof, a phenolic resin including the same, a curable composition and a cured product thereof, a semiconductor sealing material, and a printed circuit board.

Solution to Problem

As a result of thorough studies in order to achieve the above object, the present inventors found that, since a compound containing a phenolic hydroxyl group having a dinaphthofuran skeleton has high rigidity of the molecular skeleton and a high aromatic ring concentration, the heat resistance and the flame retardancy of the cured product are also excellent, and completed the present invention.

That is, the present invention relates to a compound containing a phenolic hydroxyl group having a dinaphthofuran skeleton, in which each of the two naphthylene skeletons has a hydroxyl group on the aromatic nucleus thereof.

The present invention further relates to a phenolic resin containing the compound containing a phenolic hydroxyl group.

The present invention still further relates to a preparation method of a phenolic resin, including reacting a naphthoquinone compound (Q) and a dihydroxynaphthalene compound (P) with each other in the presence of an acid catalyst.

The present invention still further relates to a phenolic resin prepared by the preparation method.

The present invention still further relates to a curable composition including the compound containing a phenolic hydroxyl group or the phenolic resin and a curing agent, as essential components.

The present invention still further relates to a cured product which is obtained by a curing reaction of the curable composition.

The present invention still further relates to a semiconductor sealing material containing the curable composition and an inorganic filler.

The present invention still further relates to a printed circuit board obtained by impregnating a reinforcement basic material with a resin composition varnished by blending the curable composition with an organic solvent, and superposing a copper foil on the resulting material, followed by heat-pressing.

Advantageous Effects of Invention

According to the present invention, it is possible to provide a compound containing a phenolic hydroxyl group which exhibits excellent heat resistance and flame retardancy in terms of a cured product thereof, a phenolic resin including the same, a curable composition and a cured product thereof, a semiconductor sealing material, and a printed circuit board.

DESCRIPTION OF EMBODIMENTS

Hereinafter, the present invention will be described in detail.

A compound containing a phenolic hydroxyl group of the present invention has a dinaphthofuran skeleton, in which each of the two naphthylene skeletons has a hydroxyl group on the aromatic nucleus thereof.

Since the compound containing a phenolic hydroxyl group of the present invention has a molecular structure which is rigid and has a high aromatic ring concentration, which is a dinaphthofuran structure, the heat resistance and the flame retardancy of the cured product are excellent. In general, as a method of improving the heat resistance of the cured product, a method of polyfunctionalizing an aromatic ring using a connecting agent such as a formaldehyde is known. However, in the compound polyfunctionalized by such a method, aromatic rings are connected with only one bonding chain, and thus, the bonding is easily cleaved at the time of combustion, and due to this, the flame retardancy thereof is low. In contrast, in the compound containing a phenolic hydroxyl group of the present invention, aromatic rings are fixed by both an ether bond and a direct bond, and thus, the two bonds are not easily cleaved at the time of combustion, and due to this, the flame retardancy thereof is high. Furthermore, since the compound containing a phenolic hydroxyl group of the present invention has two naphthalene skeletons in the molecular structure, the aromatic ring concentration is high, and extremely excellent flame retardancy is exhibited.

In addition, it is preferable that the compound containing a phenolic hydroxyl group of the present invention has a dinaphthofuran skeleton, each of the two naphthylene skeletons has a hydroxyl group on the aromatic nucleus thereof, and at least one of the two naphthylene skeletons has a hydroxyl group at the para position with respect to the carbon atom to which an oxygen atom, forming a furan ring, is bonded from the viewpoint of excellent reactivity and more excellent heat resistance and flame retardancy of the cured product.

As such a compound containing a phenolic hydroxyl group, the compound having the molecular structure represented by the following Structural Formula (I) is exemplified.

[Chem. 2]

(I)

In the formula, each of $R^1$ and $R^2$ is independently any one of an alkyl group having 1 to 4 carbon atoms, an alkoxy group having 1 to 4 carbon atoms, an aryl group, and an aralkyl group, and each of m and n is independently an integer of 0 to 4; in a case where m or n is 2 or greater, a plurality of $R^1$'s or $R^2$'s may be the same as or different from each other; and x and y represent the bonding points to the naphthalene ring, and are bonded to the carbons adjacent to each other so as to form a furan ring.

As the compound containing a phenolic hydroxyl group represented by General Formula (I), a compound prepared by a method in which a naphthoquinone compound (Q) and a dihydroxynaphthalene compound (P) are reacted with each other at a temperature range of 40° C. to 180° C. under acid catalytic conditions is exemplified.

In the case of preparing the compound containing a phenolic hydroxyl group of the present invention by such a method, it is possible to selectively prepare an arbitrary component according to the reaction conditions, or it is possible to prepare a phenolic resin which is a mixture of a plurality of compounds containing a phenolic hydroxyl group. In addition, only the arbitrary component is isolated from the phenolic resin which is a mixture and may be used.

As the naphthoquinone compound (Q), 1,4-naphthoquinone and a compound obtained by substituting an atom or a group on 1,4-naphthoquinone with one or a plurality of an alkyl group having 1 to 4 carbon atoms, an alkoxy group having 1 to 4 carbon atoms, an aryl group, or an aralkyl group are exemplified. These may be used alone respectively, or two or more types may be used in combination. Among these, 1,4-naphthoquinone is preferable since a compound containing a phenolic hydroxyl group which exhibits excellent flame retardancy and heat resistance in terms of the cured product is obtained.

Examples of the dihydroxynaphthalene compound (P) include 1,4-dihydroxynaphthalene, 1,5-dihydroxynaphthalene, 1,6-dihydroxynaphthalene, 2,6-dihydroxynaphthalene, 2,7-dihydroxynaphthalene, and a compound obtained by substituting an atom or a group on the dihydroxynaphthalene with one or a plurality of an alkyl group having 1 to 4 carbon atoms, an alkoxy group having 1 to 4 carbon atoms, an aryl group, or an aralkyl group. These may be used alone respectively, or two or more types may be used in combination. Among these, 1,4-dihydroxynaphthalene, 1,5-dihydroxynaphthalene, 1,6-dihydroxynaphthalene, 2,6-dihydroxynaphthalene, or 2,7-dihydroxynaphthalene is preferable, and 2,7-dihydroxynaphthalene is particularly preferable since a compound containing a phenolic hydroxyl group which exhibits excellent heat resistance and flame retardancy in terms of the cured product is obtained.

At this time, since the compound containing a phenolic hydroxyl group represented by Structural Formula (1) can be prepared with high efficiency, the reaction proportion between the naphthoquinone compound (Q) and the dihydroxynaphthalene compound (P) is preferably a proportion in which the dihydroxynaphthalene compound (P) is within a range of 0.1 mole to 10.0 moles with respect to 1 mole of the naphthoquinone compound (Q).

The compound containing a phenolic hydroxyl group of the present invention having a dinaphthofuran structure can be prepared with high efficiency by the reaction between the naphthoquinone compound (Q) and the dihydroxynaphthalene compound (P) under acid catalytic conditions. Examples of the acid catalyst used here include inorganic acids such as hydrochloric acid, sulfuric acid, and phosphoric acid, organic acids such as methanesulfonic acid, p-toluenesulfonic acid, and oxalic acid, or Lewis acids such as boron trifluoride, anhydrous aluminum chloride, and zinc chloride. The acid catalyst is preferably used in the amount of 5.0% by mass or less with respect to the total mass of the naphthoquinone compound (Q) and the dihydroxynaphthalene compound (P).

In addition, the reaction is preferably performed in solvent-free conditions; however, the reaction may be performed in an organic solvent, as necessary. Examples of the organic solvent used here include methyl cellosolve, isopropyl alcohol, ethyl cellosolve, toluene, xylene, and methyl isobutyl ketone. In the case of using one of the organic solvents described above, the organic solvent is preferably used in a proportion within a range of 50 parts by mass to 200 parts by mass with respect to the total 100 parts by mass of the naphthoquinone compound (Q) and the dihydroxynaphthalene compound (P), from the viewpoint of improvement of reaction efficiency.

After the reaction of the naphthoquinone compound (Q) with the dihydroxynaphthalene compound (P) ends, drying under reduced pressure is performed, whereby a desired compound containing a phenolic hydroxyl group or phenolic resin can be obtained.

As the compound containing a phenolic hydroxyl group represented by Structural Formula (I), more specifically, the compound containing a phenolic hydroxyl group represented by any one of the following Structural Formulas (I-1) to (I-9) is exemplified.

[Chem. 3]

(I-1)

(I-2)

(I-3)

(I-4)

(I-5)

(I-6)

(I-7)

(I-8)

(I-9)

Among these, the compound represented by Structural Formula (I-8) or (I-9), that is, a compound containing a phenolic hydroxyl group obtained by using 2,7-dihydroxynaphthalene as the dihydroxynaphthalene compound (P) is preferable since the heat resistance and the flame retardancy of the cured product are more excellent.

A phenolic resin containing the compound containing a phenolic hydroxyl group represented by Structural Formula (I) may contain a compound containing a phenolic hydroxyl group other than the compounds containing a phenolic hydroxyl group described above. In a case where the phenolic resin contains a compound containing a phenolic hydroxyl group other than the dinaphthofuran compound represented by Structural Formula (I), the content of the dinaphthofuran compound represented by Structural Formula (I) in the phenolic resin is preferably within a range of 5% to 80% in area ratio in a GPC measurement.

As a specific example of other compounds containing a phenolic hydroxyl group, the polyfunctional compound represented by the following Structural Formula (II) or (III) is preferable since a phenolic resin which has high heat resistance is obtained.

[Chem. 4]

In the formula, k is 1 or 2; and x and y in Formula (III) represent the bonding points to the naphthalene ring, and are bonded to the carbons adjacent to each other so as to form a furan ring.

In a case where the phenolic resin contains a polyfunctional compound represented by Structural Formula (II), the content is preferably within a range of 2% to 60% in area ratio in a GPC measurement. In addition, in a case where the phenolic resin contains a polyfunctional compound represented by Structural Formula (III), the content is preferably within a range of 2% to 40% in area ratio in a GPC measurement.

Moreover, in the present invention, the content of the respective components in the phenolic resin refers to a proportion of the peak area of each component with respect to the total peak area of the phenolic resin, which is calculated from GPC measurement data under the following conditions.

<GPC Measurement Conditions>
Measurement apparatus: "HLC-8220 GPC" manufactured by Tosoh Corporation
Column: guard column "HXL-L" manufactured by Tosoh Corporation
+"TSK-GEL G2000HXL" manufactured by Tosoh Corporation
+"TSK-GEL G2000HXL" manufactured by Tosoh Corporation
+"TSK-GEL G3000HXL" manufactured by Tosoh Corporation
+"TSK-GEL G4000HXL" manufactured by Tosoh Corporation
Detector: RI (differential refractometer)
Data processing: "GPC-8020 model II Version 4.10" manufactured by Tosoh Corporation
Measurement Conditions:

| | |
|---|---|
| column temperature | 40° C. |
| eluent | tetrahydrofuran |
| flow rate | 1.0 ml/min |

Standard: according to the measurement manual of the "GPC-8020 model II Version 4.10", the following monodisperse polystyrene of which the molecular weight is known is used.

(Polystyrene Used)
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
Sample: a solution (50 μl) obtained by filtering a tetrahydrofuran solution of 1.0% by mass in terms of the resin solid content through a microfilter.

In a phenolic resin including the compound containing a phenolic hydroxyl group of the present invention, the hydroxyl equivalent is preferably within a range of 100 g/eq to 200 g/eq from the viewpoint of excellent curing properties.

The curable composition of the present invention contains the compound containing a phenolic hydroxyl group described above or a phenolic resin including the same, and a curing agent as essential components. As the curing agent, an epoxy resin is exemplified.

Specific examples of the epoxy resin used here include naphthalene skeleton-containing epoxy resins such as 1,6-diglycidyloxy naphthalene, 2,7-diglycidyloxy naphthalene, an α-naphthol novolak type epoxy resin, a β-naphthol novolak type epoxy resin, polyglycidyl ether of α-naphthol/β-naphthol co-condensed novolak, a naphthol aralkyl type epoxy resin, and 1,1-bis(2,7-diglycidyloxy-1-naphthyl)alkane; bisphenol type epoxy resins such as a bisphenol A type epoxy resin and a bisphenol F type epoxy resin; biphenyl type epoxy resins such as a biphenyl type epoxy resin and a tetramethyl biphenyl type epoxy resin; novolak type epoxy resins such as a phenol novolak type epoxy resin, a cresol novolak type epoxy resin, a bisphenol A novolak type epoxy resin, a bisphenol F novolak type epoxy resin, an epoxidized product of a condensate of a phenol-based compound and an aromatic aldehyde having a phenolic hydroxyl group, and a biphenyl novolak type epoxy resin; triphenylmethane type epoxy resins; tetraphenyl ethane type epoxy resins; dicyclopentadiene-phenol addition reaction type epoxy resins; phenol aralkyl type epoxy resins; phosphorus atom-containing epoxy resins; and modified epoxy resins of the present invention.

In the case of using an epoxy resin as a curing agent, the blending proportion between the compound containing a phenolic hydroxyl group or the phenolic resin and the epoxy resin is preferably a proportion in which the equivalent ratio (phenolic hydroxyl group/epoxy group) of the phenolic hydroxyl group in the compound containing a phenolic hydroxyl group or the phenolic resin to the epoxy group in the epoxy resin is 1/0.5 to 1/1.5 since reactivity and heat resistance in terms of a cured product thereof are excellent at this proportion.

In addition, in the case of using an epoxy resin as a curing agent, in addition to the compound containing a phenolic hydroxyl group or the phenolic resin of the present invention, other curing agents for epoxy resin may be used in combination. As other curing agents for epoxy resin, various known curing agents such as an amine-based compound, an amide-based compound, an acid anhydride-based compound, and a phenol-based compound are exemplified. Specifically, examples of the amine-based compound include diaminodiphenyl methane, diethylenetriamine, triethylenetetramine, diaminodiphenyl sulfone, isophoronediamine, imidazole, $BF_3$-amine complex, and guanidine derivatives, examples of the amide-based compound include dicyandiamide and a polyamide resin synthesized from a linolenic acid dimer and ethylenediamine, examples of the acid anhydride-based compound include phthalic anhydride, trimellitic anhydride, pyromellitic anhydride, maleic anhydride, tetrahydrophthalic anhydride, methyl tetrahydrophthalic anhydride, methylnadic anhydride, hexahydrophthalic anhydride, and methylhexahydrophthalic anhydride, and examples of the phenol-based compound include polyvalent phenolic compounds such as a phenol novolak resin, a cresol novolak resin, an aromatic hydrocarbon formaldehyde resin-modified phenolic resin, a dicyclopentadiene phenol adduct type resin, a phenol aralkyl resin (Xylok resin), a naphthol aralkyl resin, a triphenylol methane resin, a tetraphenylol ethane resin, a naphthol novolak resin, a naphthol-phenol co-condensed novolak resin, a naphthol-cresol co-condensed novolak resin, a biphenyl-modified phenolic resin (polyvalent phenolic compound in which a phenolic nucleus is linked by a bismethylene group), a biphenyl-modified naphthol resin (polyvalent naphthol compound in which a phenolic nucleus is linked by a bismethylene group), an aminotriazine-modified phenolic resin (polyvalent phenolic compound in which a phenolic nucleus is linked by melamine, benzoguanamine, or the like), and an alkoxy group-containing aromatic ring-modified novolak resin (polyvalent phenolic compound in which a phenolic nucleus and an alkoxy group-containing aromatic ring are linked by a formaldehyde).

In the case of using other curing agents for epoxy resin, the blending proportion between the compound containing a phenolic hydroxyl group or the phenolic resin of the present invention and other curing agents for epoxy resin is not particularly limited as long as the characteristics of the compound containing a phenolic hydroxyl group of the application which exhibits excellent heat resistance and flame retardancy in terms of a cured product thereof are not impaired, and, for example, the compound containing a phenolic hydroxyl group or the phenolic resin of the present invention is preferably within a range of 5 parts by mass to 95 parts by mass in 100 parts by mass of the total mass of both.

In addition, in the case of using other curing agents for epoxy resin, the blending proportion with the epoxy resin is preferably a proportion in which the equivalent ratio (active hydrogen atom/epoxy group) between the total of active hydrogen atoms contained in the compound containing a phenolic hydroxyl group or the phenolic resin of the present invention and other curing agent for epoxy resin, and the epoxy group contained in the epoxy resin is 1/0.5 to 1/1.5 since reactivity and heat resistance of the cured product are excellent at this proportion.

In the curable composition of the present invention, a curing promoter can also be suitably used in combination as necessary. As the curing promoter, various curing promoters can be used, and examples thereof include phosphorus-based compounds, tertiary amines, imidazoles, organic acid metal salts, Lewis acids, and amine complex salts. In particular, in the case of using the curing promoter as semiconductor sealing material applications, 2-ethyl-4-methylimidazole as the imidazole compounds, triphenylphosphine as the phosphorus-based compounds, and 1,8-diazabicyclo-[5.4.0]-undecene (DBU) as the tertiary amines are preferable from the viewpoint of excellent curing properties, heat resistance, electrical characteristics, and moisture resistance reliability.

The curable composition of the present invention described above may further contain other additive components depending on the applications or the desired performance. Specifically, for the purposes of further improving flame retardancy, a non-halogen-based flame retardant which substantially does not contain a halogen atom may be blended.

Examples of the non-halogen-based flame retardant include a phosphorus-based flame retardant, a nitrogen-based flame retardant, a silicone-based flame retardant, an inorganic flame retardant, and an organometallic salt-based flame retardant, and nothing is limited even when using these, these may be used alone, or a plurality of the same types of flame retardant may be used, and the different types of flame retardant may also be used in combination.

As the phosphorus-based flame retardant, any one of an inorganic flame retardant and an organic flame retardant can be used. Examples of the inorganic compound include red phosphorus and an inorganic nitrogen-containing phosphorus compound such as ammonium phosphates, e.g., mono-ammonium phosphate, diammonium phosphate, triammonium phosphate or ammonium polyphosphate; and amide phosphate.

In addition, the red phosphorus is preferably subjected to a surface treatment for the purpose of preventing hydrolysis or the like, and examples of the surface treatment method include (i) a method for coat-treating with an inorganic compound such as magnesium hydroxide, aluminum hydroxide, zinc hydroxide, titanium hydroxide, bismuth oxide, bismuth hydroxide, bismuth nitrate, or a mixture thereof, (ii) a method for coat-treating with a mixture of an inorganic compound such as magnesium hydroxide, aluminum hydroxide, zinc hydroxide, or titanium hydroxide, and a thermosetting resin such as a phenolic resin, and (iii) a method for doubly coat-treating the surface of a coated film of an inorganic compound such as magnesium hydroxide, aluminum hydroxide, zinc hydroxide, or titanium hydroxide with a thermosetting resin such as a phenolic resin.

Examples of the organic phosphorus-based compound include general-purpose organic phosphorus-based compounds such as a phosphoric acid ester compound, a phosphonic acid compound, a phosphinic acid compound, a phosphine oxide compound, a phosphorane compound, and an organic nitrogen-containing phosphorus compound, and cyclic organic phosphorus compounds such as 9,10-dihydro-9-oxa-10-phosphaphenanthrene-10-oxide, 10-(2,5-dihydroxyphenyl)-10H-9-oxa-10-phosphaphenanthrene-10-oxide, and 10-(2,7-dihydroxynaphthyl)-10H-9-oxa-10-phosphaphenanthrene-10-oxide, and derivatives obtained by reacting this with a compound such as an epoxy resin or a phenolic resin.

The blending amount thereof is suitably selected depending on the type of a phosphorus-based flame retardant, other components of a curable composition, and the desired degree of flame retardancy, and for example, in the case of using red phosphorus as a non-halogen-based flame retardant, the red phosphorus is preferably blended within a range of 0.1 parts by mass to 2.0 parts by mass, and in the case of using an organic phosphorus compound, the organic phosphorus compound is preferably blended within a range of 0.1 parts by mass to 10.0 parts by mass, and particularly preferably blended within a range of 0.5 parts by mass to 6.0 parts by mass, in 100 parts by mass of the curable composition obtained by blending all of a compound containing a phenolic hydroxyl group or a phenolic resin, a curing agent, and other additives, or a filler.

The blending amount thereof is suitably selected depending on the type of a phosphorus-based flame retardant, other components of a curable composition, and the desired degree of flame retardancy, and for example, in the case of using red phosphorus as a non-halogen-based flame retardant, the red phosphorus is preferably blended within a range of 0.1 parts by mass to 2.0 parts by mass, and in the case of using an organic phosphorus compound, the organic phosphorus compound is preferably blended within a range of 0.1 parts by mass to 10.0 parts by mass, and particularly preferably blended within a range of 0.5 parts by mass to 6.0 parts by mass, in 100 parts by mass of the curable composition.

In addition, in the case of using the phosphorus-based flame retardant, the phosphorus-based flame retardant may be used in combination with hydrotalcite, magnesium hydroxide, a boron compound, zirconium oxide, black dye, calcium carbonate, zeolite, zinc molybdate, or activated charcoal.

Examples of the nitrogen-based flame retardant include a triazine compound, a cyanuric acid compound, an isocyanuric acid compound, and phenothiazine, and the triazine compound, the cyanuric acid compound, or the isocyanuric acid compound is preferable.

Examples of the triazine compound include (i) aminotriazine sulfate compounds such as guanylic melamine sulfate, melem sulfate, and melam sulfate, (ii) co-condensates of a phenol-based compound such as phenol, cresol, xylenol, butylphenol, or nonylphenol, and melamines such as melamine, benzoguanamine, acetoguanamine, or formguanamine and formaldehyde, (iii) a mixture of the co-condensates of (ii) and phenolic resins such as a phenolformaldehyde condensate or the like, (iv) a product obtained by further modifying (ii) and (iii) with tung oil or isomerized linseed oil, or the like, in addition to melamine, acetoguanamine, benzoguanamine, melon, melam, succinoguanamine, ethylene dimelamine, melamine polyphosphate, and triguanamine.

Examples of the cyanuric acid compound can include cyanuric acid and melamine cyanurate.

The blending amount of the nitrogen-based flame retardant is suitably selected depending on the type of the nitrogen-based flame retardant, other components of a curable composition, and the desired degree of flame retardancy, and for example, the nitrogen-based flame retardant is preferably blended within a range of 0.05 parts by mass to 10 parts by mass, and particularly preferably blended within a range of 0.1 parts by mass to 5 parts by mass, in 100 parts by mass of the curable composition.

In addition, when using the nitrogen-based flame retardant, metal hydroxide or a molybdenum compound may be used in combination.

The silicone-based flame retardant can be used without any particular limitation as long as the silicone-based flame retardant is an organic compound containing a silicon atom, and examples thereof include silicone oil, silicone rubber, and silicone resins.

The blending amount of the silicone-based flame retardant is suitably selected depending on the type of the silicone-based flame retardant, other components of a curable composition, and the desired degree of flame retardancy, and for example, the silicone-based flame retardant is preferably blended within a range of 0.05 parts by mass to 20 parts by mass in 100 parts by mass of the curable composition. In addition, when using the silicone-based flame retardant, a molybdenum compound or alumina may be used in combination.

Examples of the inorganic flame retardant include metal hydroxides, metal oxides, metal carbonate compounds, metal powder, boron compounds, and low melting point glass.

Examples of the metal hydroxide can include aluminum hydroxide, magnesium hydroxide, dolomite, hydrotalcite, calcium hydroxide, barium hydroxide, and zirconium hydroxide.

Examples of the metal oxide can include zinc molybdate, molybdenum trioxide, zinc stannate, tin oxide, aluminum oxide, iron oxide, titanium oxide, manganese oxide, zirconium oxide, zinc oxide, molybdenum oxide, cobalt oxide, bismuth oxide, chromium oxide, nickel oxide, copper oxide, and tungsten oxide.

Examples of the metal carbonate compound can include zinc carbonate, magnesium carbonate, calcium carbonate, barium carbonate, basic magnesium carbonate, aluminum carbonate, iron carbonate, cobalt carbonate, and titanium carbonate.

Examples of the metal powder can include aluminum powder, iron powder, titanium powder, manganese powder, zinc powder, molybdenum powder, cobalt powder, bismuth powder, chromium powder, nickel powder, copper powder, tungsten powder, and tin powder.

Examples of the boron compound can include zinc borate, zinc metaborate, barium metaborate, boric acid, and borax.

Examples of the low melting point glass can include glass-like compounds such as a Ceepree (Bokusui Brown Co., Ltd.) glass, a hydrated glass $SiO_2$—$MgO$—$H_2O$, $PbO$—$B_2O_3$-based glass, a $ZnO$—$P_2O_5$—$MgO$-based glass, a $P_2O_5$—$B_2O_3$—$PbO$—$MgO$-based glass, a $P$—$Sn$—$O$—$F$-based glass, a $PbO$—$V_2O_5$—$TeO_2$-based glass, an $Al_2O_3$—$H_2O$-based glass, and lead borosilicate-based glass.

The blending amount of the inorganic flame retardant is suitably selected depending on the type of the inorganic flame retardant, other components of a curable composition, and the desired degree of flame retardancy, and for example, the inorganic flame retardant is preferably blended within a range of 0.5 parts by mass to 50 parts by mass, and particularly preferably blended within a range of 5 parts by mass to 30 parts by mass in 100 parts by mass of the curable composition.

Examples of the organometallic salt-based flame retardant include ferrocene, an acetylacetonate metal complex, an organometallic carbonyl compound, an organic cobalt salt compound, an organic sulfonic acid metal salt, and a compound obtained by an ionic bond or a coordination bond of a metal atom to an aromatic compound or a heterocyclic compound.

The blending amount of the organometallic salt-based flame retardant is suitably selected depending on the type of the organometallic salt-based flame retardant, other components of a curable composition, and the desired degree of flame retardancy, and for example, the organometallic salt-based flame retardant is preferably blended within a range of 0.005 parts by mass to 10 parts by mass in 100 parts by mass of the curable composition.

In addition, various compounding agents such as a silane coupling agent, a release agent, a pigment, and an emulsifier can be added to the curable composition of the present invention, as necessary.

In the curable composition of the present invention, an inorganic filler can be blended, as necessary.

Examples of the inorganic filler include fused silica, crystalline silica, alumina, silicon nitride, and aluminum hydroxide. Among these, the fused silica is preferable since greater amount of the inorganic filler can be blended. The fused silica can be used in any one of a crushed shape or a spherical shape; however, in order to increase the blending amount of the fused silica and to suppress increase in melt viscosity of the curable composition, spherical silica is preferably mainly used. Furthermore, in order to increase the blending amount of the spherical silica, the particle size distribution of the spherical silica is preferably suitably adjusted. The filling ratio is preferably within a range of 0.5 parts by mass to 95 parts by mass in 100 parts by mass of the curable composition.

In addition, in the case of using the curable composition of the present invention in applications such as a conductive paste, it is possible to use a conductive filler such as silver powder or copper powder.

In the case of preparing the curable composition of the present invention in a varnish for a printed circuit board, an organic solvent is preferably blended. Examples of the organic solvent capable of being used here include methyl ethyl ketone, acetone, dimethylformamide, methyl isobutyl ketone, methoxypropanol, cyclohexanone, methyl cellosolve, ethyl diglycol acetate, and propylene glycol monomethyl ether acetate, and the selection and the suitable amount to be used can be suitably selected depending on the application, and, for example, in printed circuit board applications, polar solvents such as methyl ethyl ketone, acetone, and dimethylformamide having the boiling point of 160° C. or lower are preferable, and the solvents are preferably used in a proportion in which the non-volatile content becomes 40% by mass to 80% by mass. On the other hand, in adhesive film applications for build-up, as the organic solvent, for example, ketones such as acetone, methyl ethyl ketone, and cyclohexanone, acetic acid esters such as ethyl acetate, butyl acetate, cellosolve acetate, propylene glycol monomethyl ether acetate, and carbitol acetate, carbitols such as cellosolve and butyl carbitol, aromatic hydrocarbons such as toluene and xylene, dimethylformamide, dimethylacetamide, or N-methylpyrrolidone are preferably used, and the solvents are preferably used in a proportion in which the non-volatile content becomes 30% by mass to 60% by mass.

The curable composition of the present invention is obtained by uniformly mixing the respective components described above. The curable composition of the present invention obtained by blending a compound containing a phenolic hydroxyl group or a resin, a curing agent, and as necessary, a curing promoter can be easily cured by the same methods as methods known in the related art, whereby a cured product is formed. Examples of the cured product include molded cured products such as a laminate, a cast material, an adhesive layer, a coating film, and a film.

Since the compound containing a phenolic hydroxyl group and the phenolic resin of the present invention exhibit excellent heat resistance and flame retardancy in terms of a cured product thereof, the compound containing a phenolic hydroxyl group and the phenolic resin can be used in various electronic material applications. Among these, in particular, the compound containing a phenolic hydroxyl group and the phenolic resin can be suitably used in semiconductor sealing material applications.

The semiconductor sealing material can be prepared by a method in which a mixture of a phenol component including the compound containing a phenolic hydroxyl group or the phenolic resin of the present invention, a curing agent, and a filler is sufficiently mixed until it becomes uniform using an extruder, a kneader, or a roll. As the filler used here, the inorganic fillers described above are exemplified, and, as described above, the filler is preferably used within a range of 0.5 parts by mass to 95 parts by mass in 100 parts by mass of the curable composition. Among these, the filler is preferably used within a range of 70 parts by mass to 95 parts by mass, and particularly preferably used within a range of 80 parts by mass to 95 parts by mass, since flame retardancy, moisture resistance, and soldering crack resistance are improved, and a linear expansion coefficient can be reduced.

As a method for molding a semiconductor package using the obtained semiconductor sealing material, a method in which the semiconductor sealing material is formed using a casting, a transfer forming machine, or an injection molding machine, and the resultant product is heated for 2 hours to 10 hours under temperature conditions of 50° C. to 200° C. is exemplified, and by such a method, it is possible to obtain a semiconductor device which is a molded product.

In addition, in production of a printed circuit board using the compound containing a phenolic hydroxyl group or the phenolic resin of the present invention, a method which includes impregnating a reinforcement basic material with a varnish-like curable composition including the compound containing a phenolic hydroxyl group or the phenolic resin of the present invention, a curing agent, an organic solvent, and other additives, and superposing a copper foil on the resulting material, followed by heat-pressing is exemplified. Examples of the reinforcement basic material capable of being used here include paper, glass cloth, glass nonwoven fabric, aramid paper, aramid cloth, glass mat, and glass roving cloth. In describing the method in more detail, first, the varnish-like curable composition described above is heated at a heating temperature according to the solvent species used, preferably 50° C. to 170° C., whereby prepreg is obtained which is a cured product. The mass proportion between the curable composition and the reinforcement basic material used at this time is not particularly limited; however, typically, the prepreg is preferably prepared such that the resin content in the prepreg is 20% by mass to 60% by mass. Next, the prepreg obtained in the above manner is laminated by an ordinary method, then, copper foil is suitably superposed thereon, and the resultant product is heat-pressed at 170° C. to 250° C. for 10 minutes to 3 hours under a pressure of 1 MPa to 10 MPa, whereby a desired printed circuit board is obtained.

EXAMPLES

Hereinafter, the present invention will be more specifically described using examples and comparative examples, and "parts" and "%" below are based on mass unless otherwise specifically indicated. GPC was measured under the following conditions.

GPC: the measurement conditions are as follows.
Measurement apparatus: "HLC-8220 GPC" manufactured by Tosoh Corporation
Column: guard column "HXL-L" manufactured by Tosoh Corporation
+"TSK-GEL G2000HXL" manufactured by Tosoh Corporation
+"TSK-GEL G2000HXL" manufactured by Tosoh Corporation
+"TSK-GEL G3000HXL" manufactured by Tosoh Corporation
+"TSK-GEL G4000HXL" manufactured by Tosoh Corporation Detector: RI (differential refractometer)
Data processing: "GPC-8020 model II Version 4.10" manufactured by Tosoh Corporation
Measurement conditions: column temperature 40° C.
  eluent: tetrahydrofuran
  flow rate 1.0 ml/min
Standard: according to the measurement manual the "GPC-8020 model II Version 4.10", the following monodisperse polystyrene of which the molecular weight is known is used.
  (Polystyrene Used)
  "A-500" manufactured by Tosoh Corporation
  "A-1000" manufactured by Tosoh Corporation
  "A-2500" manufactured by Tosoh Corporation
  "A-5000" manufactured by Tosoh Corporation
  "F-1" manufactured by Tosoh Corporation
  "F-2" manufactured by Tosoh Corporation
  "F-4" manufactured by Tosoh Corporation
  "F-10" manufactured by Tosoh Corporation
  "F-20" manufactured by Tosoh Corporation
  "F-40" manufactured by Tosoh Corporation
  "F-80" manufactured by Tosoh Corporation
  "F-128" manufactured by Tosoh Corporation
Sample: a solution (50 μl) obtained by filtering a tetrahydrofuran solution of 1.0% by mass in terms of the resin solid content through a microfilter.

Example 1

Preparation of Phenolic Resin (1)

Figure 1:
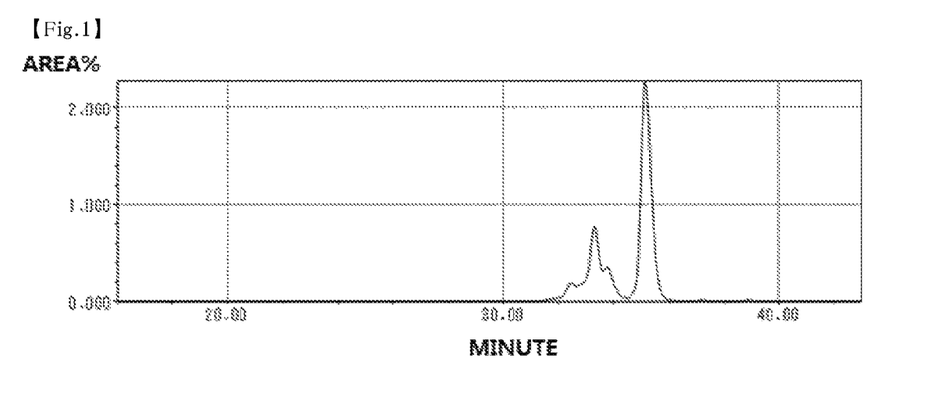
FIG. 1 is a GPC chart of a phenolic resin (1) obtained in Example 1.

160 parts by mass (1.0 mole) of 2,7-dihydroxynaphthalene, 158 parts by mass (1.0 mole) of 1,4-naphthoquinone, 6 parts by mass of para-toluenesulfonic acid, and 318 parts by mass of methyl isobutyl ketone were put into a flask equipped with a thermometer, a dropping funnel, a cooling tube, a fractionating column, and a stirrer, and the resultant product was heated from room temperature to 120° C. with stirring. After the temperature reached 120° C., stirring was performed for 3 hours for reaction. After the reaction ended, the resultant product was neutralized, and washed with 200 parts by mass of water three times. Thereafter, the resultant product was dried over under reduced pressure by being heated to 150° C., whereby 300 parts by mass of a phenolic resin (1) was obtained. A GPC chart of the obtained phenolic resin (1) is shown in FIG. 1. The hydroxyl equivalent of the phenolic resin (1) was 137 g/eq. The content of the component corresponding to the dinaphthofuran compound represented by Structural Formula (I) was 55.3%, the content of the component corresponding to the binuclear compound represented by Structural Formula (II), having the k value of 1, was 9.7%, and the content of the component corresponding to the trinuclear compound represented by Structural Formula (III) was 22.0%, calculated from the GPC chart.

Example 2

Preparation of Phenolic Resin (2)

Figure 2:
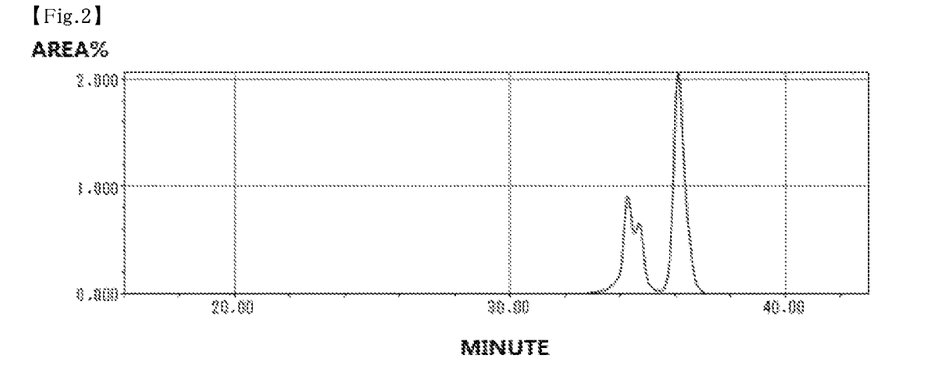
FIG. 2 is a GPC chart of a phenolic resin (2) obtained in Example 2.

160 parts by mass (1.0 mole) of 2,7-dihydroxynaphthalene, 158 parts by mass (1.0 mole) of 1,4-naphthoquinone, 6 parts by mass of para-toluenesulfonic acid, and 333 parts by mass of isopropyl alcohol were put into a flask equipped with a thermometer, a dropping funnel, a cooling tube, a fractionating column, and a stirrer, and the resultant product was heated from room temperature to 80° C. with stirring. After the temperature reached 80° C., stirring was performed for 3 hours for reaction. After the reaction ended, the resultant product was neutralized, and washed with 200 parts by mass of water three times. Thereafter, the resultant product was dried over under reduced pressure by being heated to 150° C., whereby 295 parts by mass of a phenolic resin (2) was obtained. A GPC chart of the obtained phenolic resin (2) is shown in FIG. 2. The hydroxyl equivalent of the phenolic resin (2) was 119 g/eq. The content of the component corresponding to the dinaphthofuran compound represented by Structural Formula (I) was 50.2%, the content of the component corresponding to the binuclear compound represented by Structural Formula (II), having the k value of 1, was 14.8%, and the content of the component corresponding to the trinuclear compound represented by Structural Formula (III) was 24.2%, calculated from the GPC chart.

Example 3

Preparation of Phenolic Resin (3)

Figure 3:
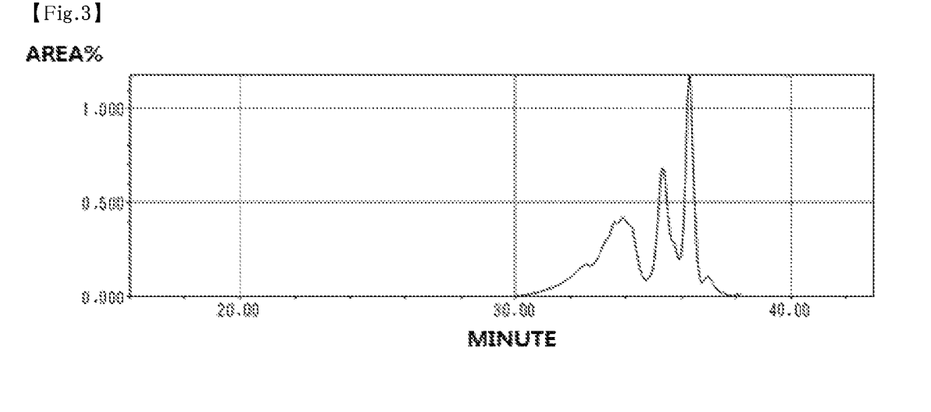
FIG. 3 is a GPC chart of a phenolic resin (3) obtained in Example 3.

160 parts by mass (1.0 mole) of 1,5-dihydroxynaphthalene, 158 parts by mass (1.0 mole) of 1,4-naphthoquinone, 6 parts by mass of para-toluenesulfonic acid, and 333 parts by mass of isopropyl alcohol were put into a flask equipped with a thermometer, a dropping funnel, a cooling tube, a fractionating column, and a stirrer, and the resultant product was heated from room temperature to 80° C. with stirring. After the temperature reached 80° C., stirring was performed for 3 hours for reaction. After the reaction ended, the resultant product was neutralized, and washed with 200 parts by mass of water three times. Thereafter, the resultant product was dried over under reduced pressure by being heated to 150° C., whereby 292 parts by mass of a phenolic resin (3) was obtained. A GPC chart of the obtained phenolic resin (3) is shown in FIG. 3. The hydroxyl equivalent of the phenolic resin (3) was 132 g/eq. The content of the component corresponding to the dinaphthofuran compound represented by Structural Formula (I), calculated from the GPC chart, was 24.1%.

Examples 4 to 6 and Comparative Example 1

Various evaluation tests were performed on the phenolic resins (1) to (3) obtained above in the following manner. As a sample for comparison, the following phenolic resin was used. Phenolic resin (1'): biphenyl aralkyl type phenolic resin described in Example 1 of PTL 1 ("MEH-7851SS" manufactured by MEIWA PLASTIC INDUSTRIES, LTD., hydroxyl equivalent of 200 g/eq)
  <Evaluation of Heat Resistance>
  1) Production of Evaluation Sample
  Any one of the phenolic resins (1) to (3), and (1'), a cresol novolak type epoxy resin ("N-655-EXP-S" manufactured by DIC Corporation, epoxy equivalent of 200 g/eq) as a curing agent, and triphenylphosphine (hereinafter, abbreviated as "TPP") as a curing promoter were blended according to the composition ratios shown in the following Table 1, whereby curable compositions were obtained. Each of these was poured into a mold of 11 cm×9 cm×2.4 mm and molded at a temperature of 150° C. for 10 minutes using a press. After the molded product was taken out from the mold, the molded product was cured at a temperature of 175° C. for 5 hours, whereby an evaluation sample was obtained.
  2) Measurement of Glass Transition Temperature
  A measurement of the temperature at which the change in elastic modulus becomes maximum (at which tan δ change ratio is the greatest) was performed on the evaluation sample using a viscoelasticity measuring apparatus (DMA: solid viscoelasticity measuring apparatus RSAII manufactured by Rheometric Scientific Inc., rectangular tension method; frequency of 1 Hz, temperature raising rate of 3° C./min), and this is evaluated as the glass transition temperature. The results are shown in Table 1.

TABLE 1

|  | Example 4 | Example 5 | Example 6 | Comparative Example 1 |
|---|---|---|---|---|
| Phenolic resin (1) | 40.7 |  |  |  |
| Phenolic resin (2) |  | 37.3 |  |  |
| Phenolic resin (3) |  |  | 39.8 |  |
| Phenolic resin (1') |  |  |  | 50.0 |
| N-655-EXP-S | 59.3 | 62.7 | 60.2 | 50.0 |
| TPP | 1.0 | 1.0 | 1.0 | 1.0 |
| Heat resistance (° C.) | 193 | 197 | 186 | 143 |

<Evaluation of Flame Retardancy>

1) Production of Evaluation Sample

Anyone of the epoxy resins (1) to (3), and (1'), a cresol novolak type epoxy resin ("N-655-EXP-S" manufactured by DIC Corporation, epoxy equivalent of 200 g/eq) as a curing agent, triphenylphosphine (hereinafter, abbreviated as "TPP") as a curing promoter, spherical silica ("FB-5604" manufactured by Denki Kagaku Kogyo Kabushiki Kaisha) as an inorganic filler, a coupling agent ("KBM-403" manufactured by Shin-Etsu Chemical Co., Ltd.) as a silane coupling agent, carnauba wax ("PEARL WAX No. 1-P" manufactured by Cerarica Noda Co., Ltd), carbon black were blended according to the composition ratios shown in the following Table 2, and the resultant products were melted and kneaded at a temperature of 85° C. for 5 minutes using a two roll, whereby curable compositions were obtained. Using the obtained curable composition, a sample having a size of the width of 12.7 mm, the length of 127 mm, and the thickness of 1.6 mm was molded at a temperature of 175° C. for 90 seconds using a transfer molding machine, and the sample was postcured at a temperature of 175° C. for 5 hours, whereby an evaluation sample was obtained.

2) Evaluation of Flame Retardancy

A combustion test was performed on the five samples for evaluation having a thickness of 1.6 mm obtained in the above according to the UL-94 test method. The results are shown in Table 2.

Flame Retardant Test Class

TABLE 2

|  | Example 4 | Example 5 | Example 6 | Comparative Example 1 |
|---|---|---|---|---|
| Phenolic resin (1) | 48.0 |  |  |  |
| Phenolic resin (2) |  | 44.0 |  |  |
| Phenolic resin (3) |  |  | 46.9 |  |
| Phenolic resin (1') |  |  |  | 59.0 |
| N-655-EXP-S | 70.0 | 74.0 | 71.1 | 59.0 |
| TPP | 2 | 2 | 2 | 2 |
| Spherical silica | 870 | 870 | 870 | 870 |
| Coupling agent | 4 | 4 | 4 | 4 |

TABLE 2-continued

|  | Example 4 | Example 5 | Example 6 | Comparative Example 1 |
|---|---|---|---|---|
| Carnauba wax | 4 | 4 | 4 | 4 |
| Carbon black | 2 | 2 | 2 | 2 |
| Flame retardant test class |  |  |  |  |
| V-0 | V-0 | V-0 | V-0 | V-1 |
| *1 | 6 | 5 | 7 | 14 |
| *2 | 20 | 18 | 40 | 76 |

The invention claimed is:

1. A curable composition, comprising as essential components: a compound containing a phenolic hydroxyl group, which has a dinaphthofuran skeleton, wherein each of the two naphthylene skeletons has a hydroxyl group on an aromatic nucleus thereof, and a curing agent.

2. A cured product obtained by a curing reaction of the curable composition according to claim 1.

3. A semiconductor sealing material, comprising: the curable composition according to claim 1; and an inorganic filler.

4. A printed circuit board obtained by impregnating a reinforcement basic material with a resin composition varnished by blending the curable composition according to claim 1 with an organic solvent, and superposing a copper foil on the resulting material, followed by heat-pressing.

5. A curable composition according to claim 1, wherein at least one of the two naphthylene skeletons has a hydroxyl group at the para position with respect to a carbon atom to which an oxygen atom, forming a furan ring, is bonded.

6. A curable composition according to claim 1, wherein the compound has a molecular structure represented by the following Structural Formula (I):

[Chem. 1]

wherein each of $R^1$ and $R^2$ is independently any one of an alkyl group having 1 to 4 carbon atoms, an alkoxy group having 1 to 4 carbon atoms, an aryl group, and an aralkyl group, and each of m and n is independently an integer of 0 to 4, in a case where m or n is 2 or greater, a plurality of $R^1$'s or $R^2$'s may be the same as or different from each other, and x and y each represent a bonding point on the naphthalene ring and are bonded to the carbons adjacent to each other so as to form a furan ring.

7. A compound containing a phenolic hydroxyl group, which has a dinaphthofuran skeleton, wherein each of the two naphthylene skeletons has a hydroxyl group on an aromatic nucleus thereof, wherein at least one of the two naphthylene skeletons has a hydroxyl group at the para position with respect to a carbon atom to which an oxygen atom, forming a furan ring, is bonded, and at least one of the naphthylene skeleton is selected from a group consisting of 1,5-dihydroxynaphthalene, 1,6-dihydroxynaphthalene, 2,6- dihydroxynaphthalene, 2,7-dihydroxynaphthalene, and mixtures thereof; wherein each of two naphthylene skeletons further contains 0 to 4 of $R^1$ or $R^2$ substituents, and $R^1$ and $R^2$ is independently any one of an alkyl group having 1 to 4 carbon atoms, an alkoxy group having 1 to 4 carbon atoms, an aryl group, and an aralkyl group, in a case where the substituents on one naphthylene skeleton is 2 or greater, a plurality of $R^1$'s or $R^2$'s may be the same as or different from each other.

8. The compound containing a phenolic hydroxyl group according to claim 7, which is selected from the following compounds and mixtures thereof:

(I-2)

(I-3)

(I-4)

(I-5)

(I-6)

(I-7)

(I-8)

(I-9)

* * * * *